United States Patent
Lipshitz et al.

[11] Patent Number: 6,066,171
[45] Date of Patent: May 23, 2000

[54] INTRAOCULAR LENS WITH PIVOTING TELESCOPE

[75] Inventors: Isaac Lipshitz, Herzelia Pituach; Eli Aharoni, Rishon le Zion; Yosef Gross, Moshav Mazor, all of Israel

[73] Assignee: Visioncare Ltd., Yehud, Israel

[21] Appl. No.: 09/229,500

[22] Filed: Jan. 11, 1999

Related U.S. Application Data

[63] Continuation of application No. 09/088,464, Jun. 1, 1998, abandoned.
[51] Int. Cl.[7] .................................................. A61F 2/16
[52] U.S. Cl. .................................... 623/6.18; 623/6.34
[58] Field of Search ......................... 623/6, 6.18, 6.32, 623/6.34, 6.35, 6.36

[56] References Cited

U.S. PATENT DOCUMENTS 5,562,731 10/1996 Cumming .................................. 623/6

FOREIGN PATENT DOCUMENTS

| 0 094 158 | 11/1983 | European Pat. Off. . |
| 0 162 573 A2 | 11/1985 | European Pat. Off. ............... 623/6 |
| 0 897 702 | 2/1999 | European Pat. Off. . |

Primary Examiner—David H. Willse
Attorney, Agent, or Firm—Darby & Darby

[57] ABSTRACT

An intraocular lens (IOL) implant for implantation in an eye having a capsular bag, the implant including a carrying member adapted to be attached to the capsular bag, and characterized by a telescope being pivotally attached to the carrying member.

19 Claims, 4 Drawing Sheets

INTRAOCULAR LENS WITH PIVOTING TELESCOPE

This is a continuation of application Ser. No. 09/088,464, filed Jun. 1, 1998, now abandoned. Each of these prior applications is hereby incorporated herein by reference, in its entirety.

FIELD OF THE INVENTION

The present invention relates generally to intraocular lens (IOL) implants and particularly to an intraocular lens with a telescope pivotally attached thereto.

BACKGROUND OF THE INVENTION

Intraocular inserts comprising telescopes are known. European Published Patent Application EP-A-212616 describes an intraocular lens that includes an anterior convex lens and a posterior concave lens. The contour of the lens can be selectively changed by varying the amount of fluid therein in order to change its refractive power. The lens is intended solely as a replacement for the natural lens of the eye.

U.S. Pat. No. 4,074,368 also describes an intraocular lens that includes an anterior convex lens and a posterior concave lens with high magnification proposed for the relief of conditions such as macular degeneration and diabetic retinopathy. The lens has many relatively low power lens surfaces arranged in a relatively long lens assembly which extends, when implanted, through almost the entire depth of the eye, from the pupil nearly to the retina. Implanting such a lens would necessitate major surgery. Moreover, the proposed lens does not provide a replacement for the natural lens for a wide field of view.

French Published Patent Application 2,666,735 describes an implant that includes a lens-shaped optical portion and a fastening assembly for securing the implant in the eye. The optical portion includes at least one closed internal cavity which contains a fluid or vacuum, forming a refraction chamber changing the optical properties of the lens.

Applicant/assignee's U.S. Pat. Nos. 5,354,335 and 5,391,202, the disclosures of which are incorporated herein by reference, describe intraocular inserts with a positive (converging) lens facing the anterior side of the eye and a negative (diverging) lens facing the posterior side, the two lenses forming a Galilean telescopic system. In U.S. Pat. No. 5,354,335, the lenses are assembled in a body member, the positive lens being generally flush with the anterior face of the body member. The negative lens may either be flush with the posterior face of the body member, or may project posteriorly therefrom. The body member anterior and/or posterior faces may be convex. In U.S. Pat. No. 5,391,202, the positive lens projects anteriorly from the anterior face of the body member which is preferably a soft lens constructed from a material such as a silicone.

In U.S. patent application Ser. No. 08/882,972, the disclosure of which is incorporated herein by reference, the present applicant/assignee discloses a further intraocular implant comprising a telescope body having an anterior end and a posterior end and including one or more windows sealed to the telescope body at the anterior end and/or the posterior end. There are at least two lenses disposed within the telescope body intermediate the anterior and posterior ends. The lenses may be a so-called reverse Galilean telescope, i.e., a negative lens faces the anterior side of the eye while a positive lens faces the posterior side of the eye. One of the features of the system is that the lenses are doublet lenses. The windows may be formed without optical power, or alternatively, may comprise a prism.

In U.S. patent application Ser. No. 08/882,973, the disclosure of which is incorporated herein by reference, the present applicant/assignee discloses yet another intraocular implant comprising a telescope (either Galilean or reverse Galilean) which extends through at least a portion of a lens capsule of the eye and forwardly thereof toward the anterior side of the eye, the telescope not penetrating the vitreous of the eye. The intraocular lens implant is supported within the lens capsule by loops, in the absence of a lens within the lens capsule. One of the features of the system is that the telescope may be tilted such that light from outside the eye is focused by the telescope on a low resolution but operative section of the retina. Other optional features of the system include one or more lenses having a graded index of refraction, holographic (diffusing) lenses, and/or doublet lenses which help prevent chromatic aberrations. The patent application also discloses a method for manufacturing an intraocular insert telescope employing laser fusing to join the lenses to the telescope body. Alternatively or additionally, the method employs glass particles having a low temperature melting point as a joining medium.

In order to insert a telescopic IOL of the prior art into the capsular bag, it is generally required to make an "open-sky" incision in the cornea, i.e., a relatively large access opening. However, such a large incision is sometimes traumatic and undesirable.

SUMMARY OF THE INVENTION

The present invention seeks to provide an improved telescopic lens system extending from an IOL implant wherein the implant can be inserted in the capsular bag without need for an "open-sky" incision. Specifically, the present invention provides an intraocular lens implant with a telescope pivotally attached thereto. When inserting the IOL implant, the telescope is pivoted so that it lies flat with the rest of the IOL implant, thereby providing a relatively thin structure which can be inserted through a simple incision in the cornea, such as about a 100° incision in the limbus. After implantation in the eye, the telescope is rotated to a position which permits proper viewing by the IOL patient.

There is thus provided in accordance with a preferred embodiment of the present invention an intraocular lens (IOL) implant for implantation in an eye having a capsular bag, the implant including a carrying member adapted to be attached to the capsular bag, and characterized by a telescope being pivotally attached to the carrying member.

In accordance with a preferred embodiment of the present invention the telescope has a longitudinal axis and the telescope is pivoted about a swivel axis which is non-parallel to the longitudinal axis. Preferably the swivel axis is generally orthogonal to the longitudinal axis. Preferably the telescope is pivotable generally 360° about a swivel axis.

Further in accordance with a preferred embodiment of the present invention the carrying member includes a pair of pivot members separated from each other by a cavity formed therebetween, and wherein the telescope is pivotally attached to the pivot members and is arranged to pivot in the cavity.

Still further in accordance with a preferred embodiment of the present invention the carrying member includes an anterior face and the cavity is of sufficient size such that the telescope can be pivoted to lie in the cavity in a position generally parallel to the anterior face, and the telescope can be pivoted to a position generally perpendicular to the anterior face.

Additionally in accordance with a preferred embodiment of the present invention the telescope includes a generally cylindrical body with at least one flat surface formed on a perimeter of the cylindrical body.

In accordance with a preferred embodiment of the present invention the telescope includes a generally cylindrical body with at least one flat surface formed on a perimeter of the cylindrical body, wherein when the telescope is pivoted to lie in the cavity in the position generally parallel to the anterior face, the flat surface is also generally parallel to the anterior face.

Further in accordance with a preferred embodiment of the present invention the pivot members include a pair of flexible tongues extending into the cavity. Preferably the tongues are cantilevered from a portion of the carrying member. Preferably the pivot members include a pair of flexible tongues extending into the cavity, the tongues being generally parallel to the anterior face.

Still further in accordance with a preferred embodiment of the present invention the pivot members include a pair of flexible tongues which are formed with a concave recess adapted to receive therein a correspondingly shaped convex outer surface of the telescope. The convex outer surface may be formed along an axial surface of the telescope. Additionally or alternatively, the convex outer surface may be formed along a radial surface of the telescope.

Additionally in accordance with a preferred embodiment of the present invention the telescope includes a generally cylindrical body and wherein the convex outer surface includes at least a portion of a ring attached about a perimeter of the telescope.

In accordance with a preferred embodiment of the present invention the telescope has a longitudinal axis and the telescope is pivoted about a swivel axis which is non-parallel to the longitudinal axis, and wherein each flexible tongue applies a biasing force upon the telescope, the forces being directed radially inwards towards the longitudinal axis of the telescope.

Further in accordance with a preferred embodiment of the present invention each tongue has sufficient resilience such that the forces are of sufficient magnitude to substantially fix the telescope at a selected pivoted position about the swivel axis.

Still further in accordance with a preferred embodiment of the present invention the carrying member includes at least one haptic extending therefrom for attachment to a portion of the eye.

Additionally in accordance with a preferred embodiment of the present invention the telescope includes a positive lens and a negative lens.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
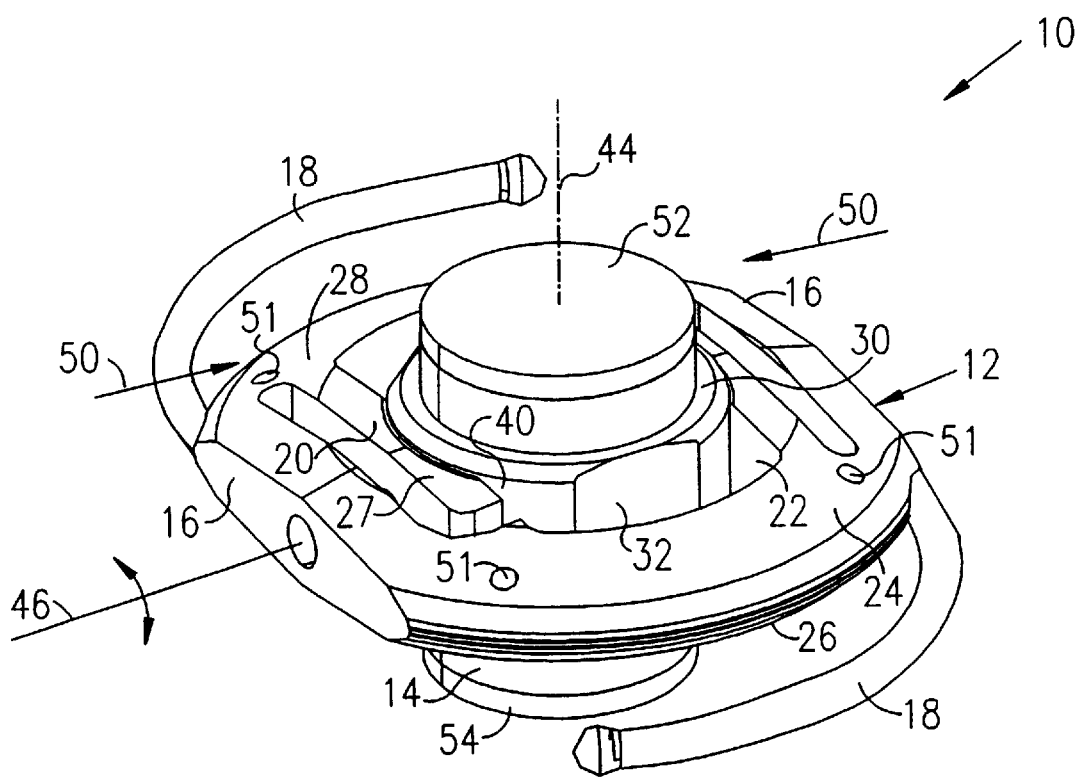
FIG. 1 is a simplified pictorial illustration of an intraocular lens implant with a telescope pivotally attached thereto, constructed and operative in accordance with a preferred embodiment of the present invention.
Figure 2:
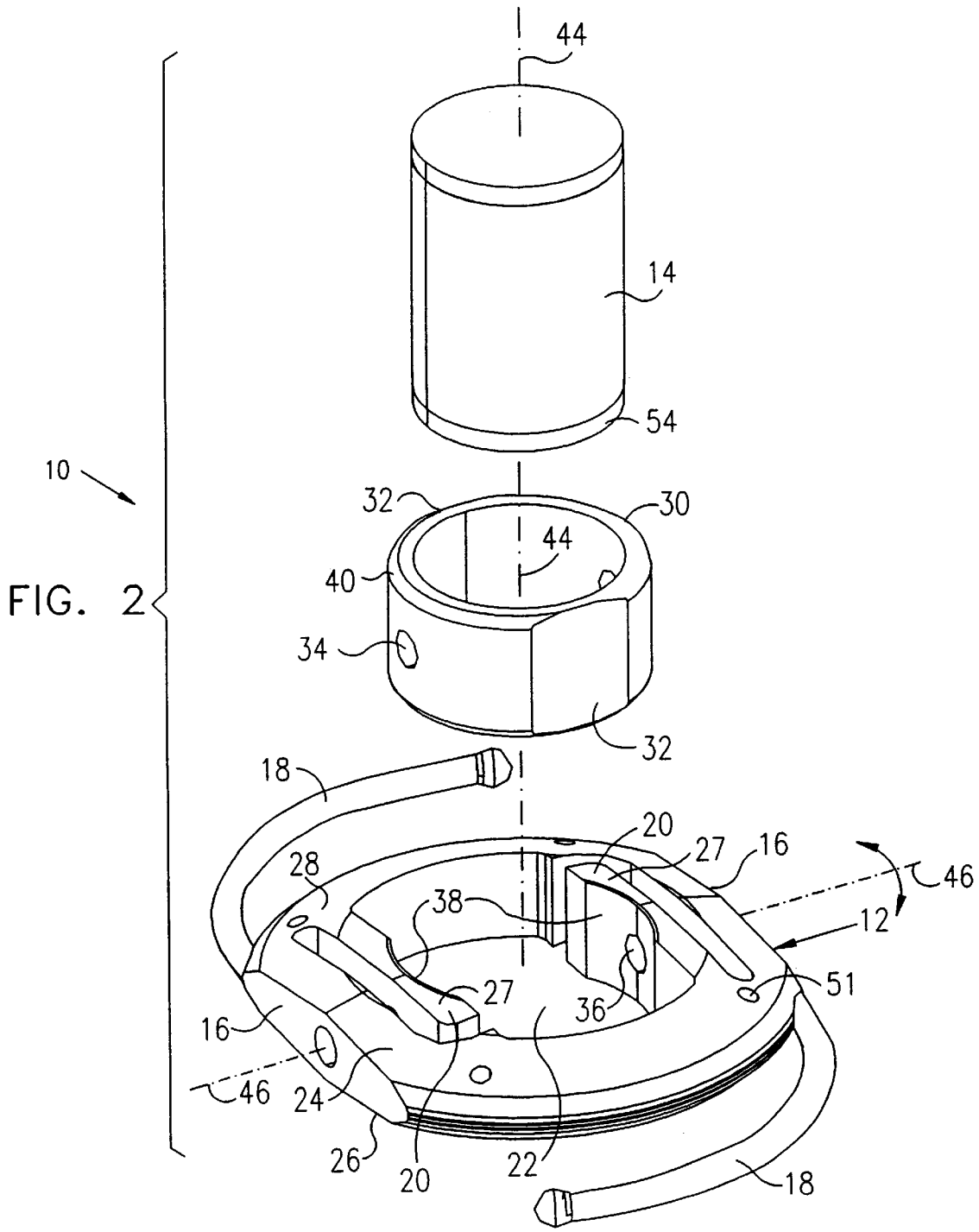
FIG. 2 is a simplified exploded illustration of the intraocular lens implant of FIG. 1.

Reference is now made to FIGS. 1 and 2 which illustrate an intraocular lens implant 10 constructed and operative in accordance with a preferred embodiment of the present invention. Lens implant 10 includes a carrying member 12 with a telescope 14 pivotally attached thereto. A suitable material for constructing all elements of lens implant 10 is polymethylmethacrylate (PMMA), for example.

Figure 4A:
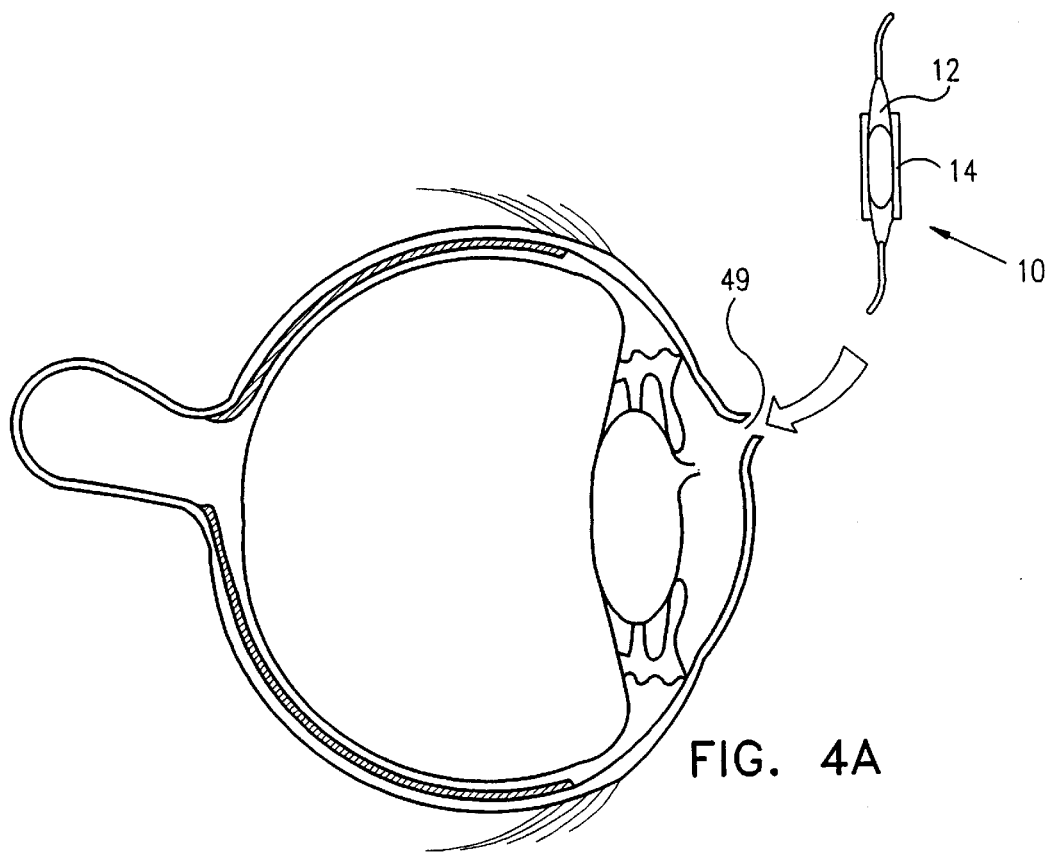
FIGS. 4A and 4B are simplified pictorial illustrations of inserting the intraocular lens implant of FIG. 1 into a capsular bag of an eye.
Figure 4B:
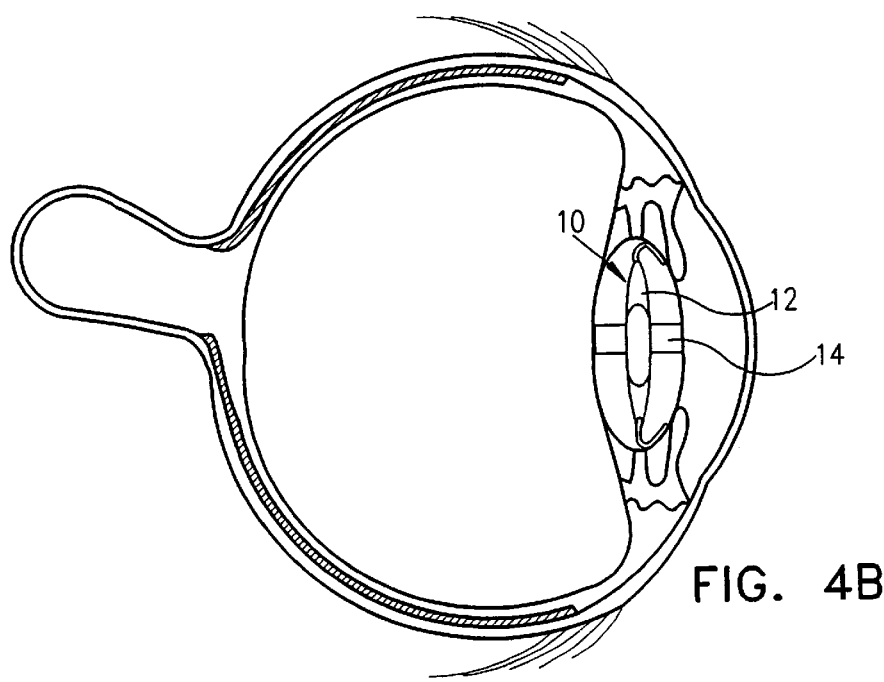

Carrying member 12 is preferably shaped generally similarly to a flat disk with truncated ends 16, and has one or more haptics 18 extending therefrom for attachment to a portion of an eye (as seen in FIGS. 4A and 4B). Carrying member 12 preferably includes a pair of pivot members 20 separated from each other by a cavity 22 formed therebetween. Cavity 22 is preferably a through bore extending from an anterior face 24 to a posterior face 26 of carry member 12. In a preferred embodiment, pivot members 20 are a pair of flexible tongues 27 which extend into cavity 22, and which are cantilevered from a portion 28 of carrying member 12. Tongues 27 are preferably generally parallel to anterior face 24 (which in turn is preferably generally parallel to posterior face 26).

Telescope 14 preferably includes a generally cylindrical body which is fixedly mounted in a ring 30. Ring 30 is preferably attached about a perimeter of telescope 14 halfway between extreme ends of telescope 14, telescope 14 and ring 30 forming a single unit. Optionally, ring 30 may be integrally formed with telescope 14 such as by molding therewith. Ring 30 is preferably formed with a pair of opposing flat surfaces 32, similar to the flats formed on a threaded nut.

Telescope 14 is pivotally attached to pivot members 20 and is arranged to pivot in cavity 22. This is preferably accomplished by forming ring 30 with a pair of generally hemispherical protrusions 34 which are rotatingly received in dimples 36 correspondingly formed in tongues 27. Telescope 14, which has a longitudinal axis 44, is pivoted about a swivel axis 46 (in the illustrated embodiment defined by a line passing through dimples 36) which is non-parallel to longitudinal axis 44. Most preferably, swivel axis 46 is generally orthogonal to longitudinal axis 44. Telescope 14 is preferably pivotable generally 360° about swivel axis 46.

Tongues 27 are preferably formed with a concave recess 38 adapted to receive therein a correspondingly shaped convex outer surface of telescope 14. In the position shown in FIG. 1, telescope 14 is positioned generally perpendicular to anterior and posterior faces 24 and 26, this normally being the position when lens implant 10 is completely installed in an eye, as is described further hereinbelow with reference to FIGS. 4A and 4B. In this position, the convex outer surface is a surface 40 formed along a width of ring 30, i.e., formed along an axial surface of telescope 14.

Figure 3:
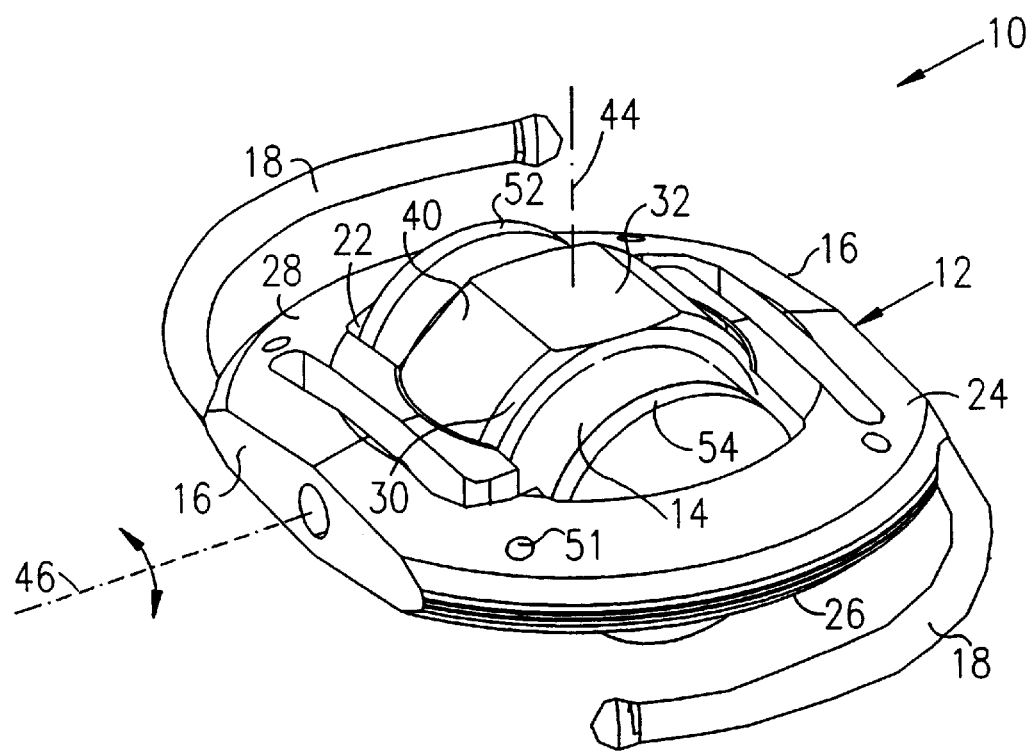
FIG. 3 is a simplified pictorial illustration of the intraocular lens implant of FIG. 1 with the telescope pivoted to lie flat with respect to a carrying member.

Reference is now made to FIG. 3 in which it is seen that cavity 22 is preferably of sufficient size such that telescope 14 can be pivoted to lie in cavity 22 in a position generally parallel to anterior and posterior faces 24 and 26, i.e., telescope 14 lies flat with respect to carrying member 12. This is the normal initial position used to install lens implant 10 in an eye, as is described further hereinbelow with reference to FIGS. 4A and 4B. In this position, the convex outer surface is the perimeter of ring 30, i.e., formed along a radial surface of telescope 14. It is noted that in this position, flat surfaces 32 are also generally parallel to anterior and posterior faces 24 and 26.

The flexible tongues 27 each apply a biasing force upon telescope 14, these forces being directed radially inwards towards the longitudinal axis 44, as indicated by arrows 50 in FIGS. 1 and 3. Preferably each tongue 27 has sufficient resilience such that these biasing forces are of sufficient magnitude to substantially fix telescope 14 at a selected pivoted position about swivel axis 46. For example, in FIG. 1, the biasing forces maintain telescope 14 such that its longitudinal axis 44 is generally perpendicular to anterior and posterior faces 24 and 26, whereas in the position of FIG. 3, the biasing forces maintain telescope 14 such that longitudinal axis 44 is generally parallel to faces 24 and 26.

Reference is now made to FIGS. 4A and 4B which illustrate inserting lens implant 10 into a capsular bag of an eye. As seen in FIG. 4A, telescope 14 is pivoted to the position shown in FIG. 3 wherein the overall thickness of implant 10 is relatively thin due to the "lying" position of telescope 14. The flat surfaces 32 formed in ring 30 further reduce the overall thickness. Because implant 10 is thin in this position, implant 10 may be inserted with a relatively simple incision 49 in the cornea, such as about a 100° incision in the limbus, instead of the much larger "open-sky" incision used generally in prior art telescopic implants. After insertion, as seen in FIG. 4B, telescope 14 may be rotated by a tool (not shown) to the position shown in FIG. 1.

As is known in the art, it may be necessary to adjust the orientation of implant 10 after placement in the eye, such as by rotating implant 10 about axis 44, this procedure sometimes being popularly referred to as "dialing". As seen in FIGS. 1–3, carrying member 12 is preferably formed with a plurality of holes 51. A suitable tool (not shown) may be inserted in any of holes 51 and then used to rotate implant 10 about axis 44.

Telescope 14 may include any lens system. For example, as seen in FIG. 1, telescope 14 may include a positive lens 52 and a negative lens 54. Since telescope 14 is preferably pivotable generally 360° about swivel axis 46, it is a particular feature of the present invention that telescope 14 can be rotated, after installation in the eye, to be a Galilean telescope (having an anteriorly positioned positive lens and a posteriorly positioned negative lens) or instead a reverse Galilean (having an anteriorly positioned negative lens and a posteriorly positioned positive lens).

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An intraocular lens (IOL) implant for implantation in an eye having a capsular bag, the implant comprising:
   a carrying member configured to be attached to said capsular bag; and
   a telescope pivotally attached to said carrying member, said telescope comprising a generally cylindrical body with at least one flat surface formed on a perimeter of said cylindrical body.

2. The implant according to claim 1 and wherein said telescope has a longitudinal axis and said telescope is pivoted about a swivel axis which is non-parallel to said longitudinal axis.

3. The implant according to claim 2 and wherein said swivel axis is generally orthogonal to said longitudinal axis.

4. The implant according to claim 1 and wherein said telescope is pivotable generally 360° about a swivel axis.

5. The implant according to claim 4 and wherein said telescope comprises a positive lens and a negative lens.

6. The implant according to claim 1 and wherein said carrying member comprises a pair of pivot members separated from each other by a cavity formed therebetween, and wherein said telescope is pivotally attached to said pivot members and is arranged to pivot in said cavity.

7. The implant according to claim 6 and wherein said carrying member comprises an anterior face and said cavity is of sufficient size such that said telescope can be pivoted to lie in said cavity in a position generally parallel to said anterior face, and said telescope can be pivoted to a position generally perpendicular to said anterior face.

8. The implant according to claim 7 wherein when said telescope is pivoted to lie in said cavity in the position generally parallel to said anterior face, said flat surface is also generally parallel to said anterior face.

9. The implant according to claim 7 and wherein said pivot members comprise a pair of flexible tongues extending into said cavity, said tongues being generally parallel to said anterior face.

10. The implant according to claim 6 and wherein said pivot members comprise a pair of flexible tongues extending into said cavity.

11. The implant according to claim 10 and wherein said tongues are cantilevered from a portion of said carrying member.

12. The implant according to claim 10 and wherein said telescope has a longitudinal axis and said telescope is pivoted about a swivel axis which is non-parallel to said longitudinal axis, and wherein each said flexible tongue applies a biasing force upon said telescope, said forces being directed radially inwards towards the longitudinal axis of said telescope.

13. The implant according to claim 12 and wherein each said tongue has sufficient resilience such that said forces are of sufficient magnitude to substantially fix said telescope at a selected pivoted position about said swivel axis.

14. The implant according to claim 6 and wherein said pivot members comprise a pair of flexible tongues which are formed with a concave recess adapted to receive therein a correspondingly shaped convex outer surface of said telescope.

15. The implant according to claim 14 and wherein said convex outer surface is formed along an axial surface of said telescope.

16. The implant according to claim 14 and wherein said convex outer surface is formed along a radial surface of said telescope.

17. The implant according to claim 16 and wherein said telescope comprises a generally cylindrical body and wherein said convex outer surface comprises at least a portion of a ring attached about a perimeter of said telescope.

18. The implant according to claim 1 and wherein said carrying member comprises at least one haptic extending therefrom for attachment to a portion of said eye.

19. The implant according to claim 1 and wherein said telescope comprises a positive lens and a negative lens.

* * * * *